(12) United States Patent
Laheurte et al.

(10) Patent No.: US 9,464,344 B2
(45) Date of Patent: Oct. 11, 2016

(54) METHOD FOR THE THERMOMECHANICAL TREATMENT OF A TITANIUM ALLOY, AND RESULTING ALLOY AND PROSTHESIS

(71) Applicants: UNIVERSITE DE LORRAINE, Nancy (FR); ECOLE NATIONALE D'INGENIEURS DE METZ (ENIM), Metz (FR); ARTS, Paris (FR); INSTITUT NATIONAL DES SCIENCES APPLIQUEES DE RENNES (INSA DE RENNES), Rennes (FR); CENTRE NATIONAL DE LA RECHERCHE SCIENTIFIQUE (CNRS), Paris (FR)

(72) Inventors: Pascal Laheurte, Forbach (FR); Frédéric Prima, Paris (FR); Thierry Gloriant, Mouaze (FR); Wafa Elmay, Metz (FR); André Eberhardt, Metz (FR); Etienne Patoor, Longevilles les Metz (FR)

(73) Assignees: UNIVERSITE DE LORRAINE, Nancy (FR); ECOLE NATIONALE D INGENIEURS DE METZ (ENIM), Metz 3 (FR); ARTS, Paris (FR); INSTITUT NATIONAL DES SCIENCES APPLIQUEES DE RENNES (INSA DE RENNES), Rennes 7 (FR); NATIONAL DE LA RECHERCHE SCIENTIFIQUE (CRNS), Paris 16 (FR)

( * ) Notice: Subject to any disclaimer, the term of this patent is extended or adjusted under 35 U.S.C. 154(b) by 331 days.

(21) Appl. No.: 14/356,544

(22) PCT Filed: Nov. 7, 2012

(86) PCT No.: PCT/EP2012/071963
§ 371 (c)(1),
(2) Date: May 6, 2014

(87) PCT Pub. No.: WO2013/068366
PCT Pub. Date: May 16, 2013

(65) Prior Publication Data
US 2014/0290811 A1    Oct. 2, 2014

(30) Foreign Application Priority Data

Nov. 10, 2011 (FR) ...................... 11 60228

(51) Int. Cl.
| A61L 27/06 | (2006.01) |
| C21D 8/00 | (2006.01) |
| C22F 1/18 | (2006.01) |
| C22C 14/00 | (2006.01) |
| A61L 27/50 | (2006.01) |

(52) U.S. Cl.
CPC ............... *C22F 1/183* (2013.01); *A61L 27/06* (2013.01); *A61L 27/50* (2013.01); *C21D 8/00* (2013.01); *C22C 14/00* (2013.01)

(58) Field of Classification Search
CPC ........ C22F 1/183; A61L 27/06; A61L 27/50; C21D 8/00; C22C 14/00
See application file for complete search history.

(56) References Cited

U.S. PATENT DOCUMENTS 6,752,882 B2 * 6/2004 Lin ..................... A61L 27/06
148/421
7,722,805 B2 * 5/2010 Hao ..................... C22F 1/183
148/421

FOREIGN PATENT DOCUMENTS

EP           0437079    *  7/1991
WO       2007137772 A2     12/2007

OTHER PUBLICATIONS

International Search Report for corresponding application PCT/EP2012/071963 filed Nov. 7, 2012; Mail date Feb. 28, 2013.

*Primary Examiner* — Colleen Dunn
(74) *Attorney, Agent, or Firm* — Cantor Colburn LLP

(57) ABSTRACT

According to a thermomechanical treatment process for a titanium alloy including between 23 and 27% niobium in atomic proportion, between 0 and 10% zirconium, and between 0 and 1% oxygen, nitrogen and/or silicon, the following steps are performed:
a) an increase of a sample of the alloy to a temperature higher than 900° C.,
b) a fast quench,
c) a severe cold strain,
d) an ageing treatment at a temperature included between 200 and 600° C., the time of the ageing treatment being included between 10 seconds and 10 minutes.
Alloy obtained by this process and prostheses made from such an alloy.

11 Claims, 9 Drawing Sheets

METHOD FOR THE THERMOMECHANICAL TREATMENT OF A TITANIUM ALLOY, AND RESULTING ALLOY AND PROSTHESIS

FIELD OF THE INVENTION

The invention relates to a thermomechanical treatment process for a titanium alloy to obtain a low modulus of elasticity and a high mechanical strength. It also relates to an alloy thus obtained and a prosthesis made from this alloy, especially a dental implant.

PRIOR ART

In medicine today, prostheses are used to replace functions which are no longer ensured or are poorly ensured by the body of a patient. Thus, prostheses are made which replace a joint, such as the hip or the knee. Also, elements are attached which support the skeleton in a permanent or temporary manner. In certain configurations, the prosthesis is made of several parts some of which are similar to screws and which are housed in the bone and which allow a mechanical link between the bone and another part of the prosthesis. Also, dental implants are made which are inserted into the bone of the jaw to replace a tooth and which receive tooth prostheses. In the remainder of the description, the term prosthesis also designates dental implants.

Prostheses are frequently made of metal to confer good mechanical strength properties to them. Today, metallic prostheses are made from Cr—Co alloys, stainless steel, titanium, two-phase titanium alloys α+β (TA6V ELI) and Ni—Ti (nickel-titanium) alloys. Titanium and its alloys are mainly used for their mechanical properties and their biocompatibility. This biocompatibility is not always total as certain elements of these alloys, such as nickel, vanadium and aluminium, are considered as potentially toxic.

The improvement of the chemical biocompatibility requires a new formulation which includes only chemically biocompatible elements. For example, the elements chosen among tantalum, zirconium, niobium and titanium are considered as posing no chemical biocompatibility problems.

Other considerations must also be taken into account for making good prostheses. In the case where the prosthesis must be integrated into a bone, it is observed that the modulus of elasticity of the material of the prosthesis plays a decisive role in the success of the integration of the prosthesis. Indeed, when the prosthesis has a stiffness greater than that of the bone, a stress deviation phenomenon occurs which reduces the stresses in certain areas and concentrates them in others. In the limit cases, the bone deteriorates at the interface with the prosthesis and the anchoring of the prosthesis is not correctly achieved.

The mechanical biocompatibility consists in adapting the stiffness of the implant to that of the bone to ensure a more homogeneous transfer of the mechanical loads favourable to osteointegration. The modulus of elasticity of titanium alloys, although lower than that of steel, still remains too high (110 GPa) if it is compared with that of the biological host tissues, around 20 GPa for bone.

Among the other interesting properties of the materials for making prostheses, special attention is paid to the superelasticity and to the pseudoelasticity. Ni—Ti or titanium β alloys are especially used for their specific superelasticity or pseudoelasticity properties which confers to them a capability to return to their initial shapes or at least to have a high recoverable strain after having been submitted to a substantial strain under the effect of a stress, unlike steel which, at equal initial strain, would undergo a permanent set and would have a low recoverable strain.

The superelasticity is characterised by a strain versus stress curve such as shown on FIG. 19 and results from a phase transformation to the solid state called martensitic transformation: under the effect of a stress, a sample of this alloy, which is at rest in the austenite state, partially transforms into martensite. When the application of the stress ceases, a return to the austenitic state by reverse transformation is observed and the sample returns to its initial dimension, with however a hysteresis effect which moves the unload curve clearly under the load curve. Thus, whereas conventional metallic alloys have a maximum elastic strain of around 0.2%, alloys with superelastic properties can offer a recoverable reversible strain $\epsilon_{recoverable}$ of 10%.

The pseudoelastic effect is shown on FIG. 20. It can be seen that, after a high imposed strain $\epsilon_{imposed}$, the release of the stress causes a return according to a reverse unload curve leaving a certain plastic strain $\epsilon_{plastic}$. This specific unload curve can be explained by a combination of a return part of purely elastic type with another part of superelastic or pseudoelastic type due to the reversibility of the martensitic transformation or to the reorientation of martensite variants such as known for example in document T. W. Duerig, R. Zadno *An Engineer's Perspectives of Pseudoelasticity, Engineering aspect of SMA*, Edt. T. W Duerig, Butterworth-Heinemann Publishers, p369, London, 1990. The recoverable strain $\epsilon_{recoverable}$, which is the amplitude of the strain during unloading, results from the sum of the elastic return $\epsilon_{r1}$ and the superelastic return $\epsilon_{r2}$ and can be around 3 to 4%.

FIG. 21 shows the consequences of the pseudoelastic effect when a sample of an alloy with these properties is submitted to a succession of imposed strains and stress releases. The return according to the reverse curve mentioned above is then called linear pseudoelasticity which is repeated in almost the same manner following each imposed strain within the limits, of course, of a strain leading to failure.

Document U.S. Pat. No. 6,752,882 proposes the use of a titanium and niobium binary alloy for its biocompatibility properties. The Young's modulus of this alloy is at least 60 GPa which, again, is too far from that of the bone.

Document U.S. Pat. No. 7,722,805 B2 refers to titanium, niobium and zirconium alloys designed to improve biocompatibility. A low Young's modulus is sought by an optimisation of the chemical composition and by heat treatments. In particular, it is shown that the Young's modulus can be lowered by optimising the chemical composition and by a water quench heat treatment. A temper treatment implies an increase in the value of the Young's modulus.

Document WO 2007/137772 shows a titanium alloy consisting of 28% niobium in weight, 1% of iron in weight and 0.5% of silicon in weight. A cylindrical ingot is forged at 850° C., then held at 900° C. for one hour to form the β phase then is quenched in water. A cold strain of 60 to 95% is then given to the sample. A material with a Young's modulus of 37.5 GPa, an elastic strength of 998 MPa and an elongation at break of 10.7% is obtained.

TARGETS OF THE INVENTION

The aim of the invention is to provide a thermomechanical treatment process for a titanium alloy to obtain a very low Young's modulus and a high mechanical strength with a good chemical and mechanical biocompatibility. Its aim is also to obtain prostheses made with such an alloy.

DISCLOSURE OF THE INVENTION

With these targets in mind, the object of the invention is a thermomechanical treatment process for a titanium alloy including between 23 and 27% niobium, between 0 and 10% zirconium, and between 0 and 1% oxygen, nitrogen and/or silicon, the ratios being expressed in atomic proportions, process wherein the following steps are performed:
a) an increase in temperature of a sample of the alloy to a temperature higher than 900° C.,
b) a quench,
c) a cold strain higher than the true strain of 3,
d) an ageing treatment at a temperature included between 200 and 600° C., the time of the ageing treatment being included between 10 seconds and 10 minutes.

It can be seen that with such a process, a titanium alloy with all the required qualities is obtained, especially a low Young's modulus, a high mechanical strength and a good biocompatibility, both chemical and mechanical. More particularly, it can be seen that such an alloy is favourably sensitive to a very short ageing treatment time, that is the Young's modulus is lowered by this treatment at the same time as the mechanical strength is increased. If the ageing treatment time is increased, an increase in the Young's modulus is obtained. It can also be seen that this alloy has excellent superelasticity properties. The combination of steps a) and b) is also called solution annealing. The annealing transforms the alloy into austenitic phase β. The quench is a thermal cooling sufficiently fast to avoid initiation of the diffusion mechanism. The cold strain can be obtained by rolling, by stamping or by drawing in one or more passes. The true strain is equal to the natural log of the quotient of the dimension after strain over the initial dimension.

Particularly, step a) is preceded by a homogenisation step at a temperature greater than 1200° C. for at least 20 hours. The chemical composition is thus uniformly distributed inside the specimen.

According to the particular characteristics of the process:
at step c), the strain is included between 400 and 500% of the finished dimension,
at step c), the strain is done only on the surface of a sample; such a strain is achieved for example by shot peening or by glass bead peening.

The object of the invention is also a titanium alloy including between 23 and 27% niobium, between 0 and 10% zirconium, and between 0 and 1% oxygen, nitrogen and/or silicon, the ratios being expressed in atomic proportions, the alloy being obtained by the process such as described above and its Young's modulus being lower than 45 GPa.

Particularly:
the niobium ratio is between 24 and 26% in atomic proportions,
the zirconium ratio is 0%.

As an example, various versions of the alloy are in compliance with the invention:
the niobium ratio of the alloy is 24%, the crystallographic structure being a β phase with traces of α martensite and a ω phase after ageing treatment at 300° C.,
the niobium ratio is 24%, the crystallographic structure including a β phase, α martensite and α" martensite after an ageing treatment at 600° C.,
the niobium ratio is 26%, the crystallographic structure including a β phase and α" martensite.

The object of the invention is also a prosthesis implantable into a human or animal body, characterised in that it is made from an alloy such as described above. Such a prosthesis is, for example, a dental implant. It can also be, for example, a clip, a screw, an endovascular prosthesis, a joint or a spring.

BRIEF DESCRIPTION OF THE FIGURES

The invention will be better understood and other features and advantages of the invention will become apparent on reading the following description, the description making reference to the appended drawings where.

DETAILED DESCRIPTION

In all the examples below, the alloy production process begins by the preparation of an ingot by mixing the metals in the required proportions and by melting them in a furnace, for example a cold crucible furnace heated by magnetic induction. This guarantees a high purity of the alloy by absence of contact between the volume of liquid and the crucible. After the ingot has been moulded to a section of around 20×20 mm, it is homogenised at a temperature included between 1200 and 1300° C. for around 20 h. After cooling, the ingot is rolled to reduce its section to 10×10 mm. It is then raised to a temperature of around 900° C. and held at this temperature for 1 hour, then quenched in water. On account of the low section of the ingot, the quench is very fast and it can be qualified as a hyper quench.

EXAMPLE 1

Two samples are prepared according to the process described above, sample A1 including 24% niobium in atomic proportion, the remainder being titanium, and sample B1 including 26% niobium, the rest also being titanium.

Figure 1:
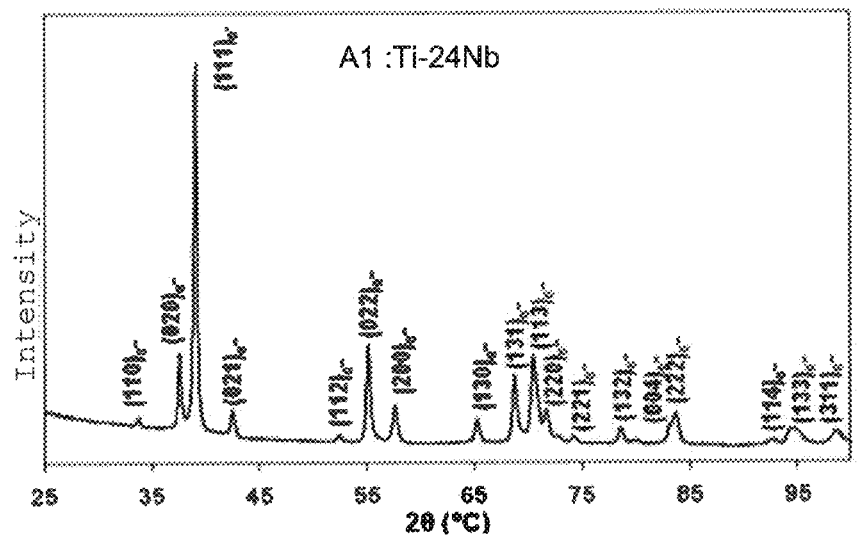
FIGS. 1 and 2 are X-ray diffraction diagrams for annealed samples.
Figure 2:
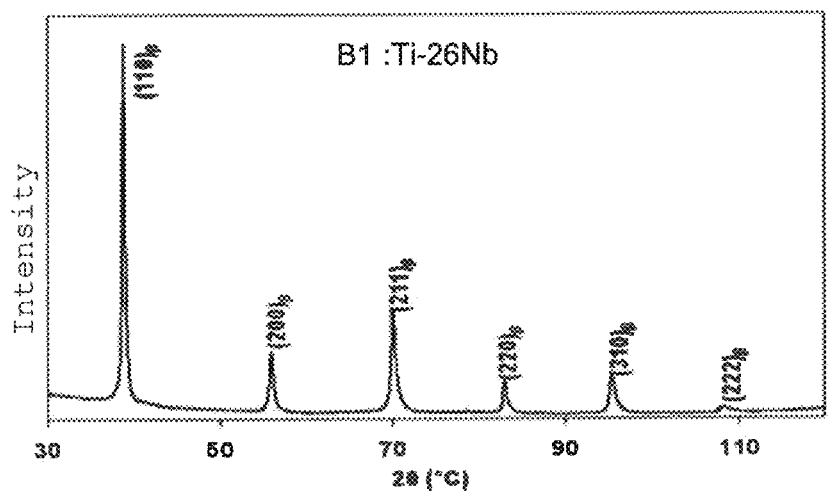
Figure 3:
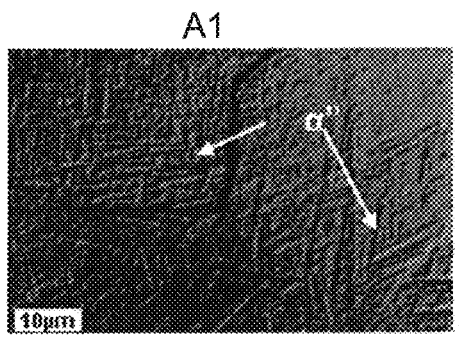
FIGS. 3 and 4 are views through optical microscope of the samples of FIGS. 1 and 2.
Figure 4:
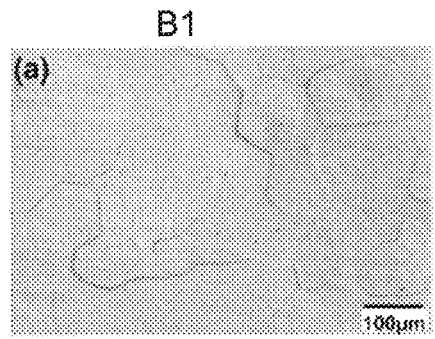

An analysis by X-ray diffraction is shown on FIGS. 1 and 2 respectively. FIG. 1 concerns sample A1 and clearly shows peaks which correspond to an α" martensite phase of orthorhombic structure, whereas sample B1, on FIG. 2, shows only peaks corresponding to a unique centred cubic β phase. FIG. 3 shows an optical microscope view of sample A1, on which α" martensite variants can be clearly seen. Two dominant characteristic morphologies are seen with the electronic transmission microscope, that is a triangular shape and a V-shape. FIG. 4, concerning sample B1, shows that the sample consists of phase β equiaxial grains of a size of around 100 μm.

Figure 5:
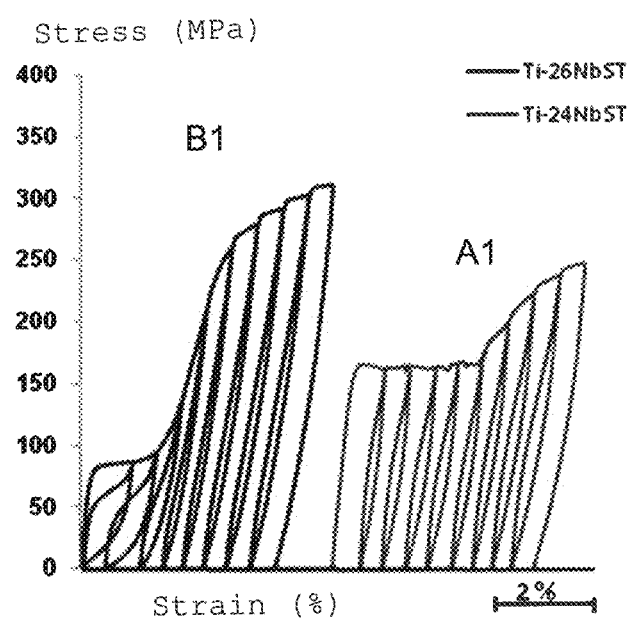
FIG. 5 shows the tension-release test curves for samples of FIGS. 1 and 2, FIGS. 6 and 7 are X-ray diffraction diagrams for the annealed and cold rolled samples which were then submitted to a short heat treatment.

Mechanical characterisation tests were conducted by doing tension-release cycles with constant strain increments. The curves relating the strain to the stress are shown on FIG. 5. Concerning sample B1, this shows a superelastic behaviour with an ultimate strength of 280 MPa. This behaviour is explained by the fact that, for this alloy, the Ms martensitic transformation temperature (270K) is lower than the ambient temperature. At ambient temperature, the alloy consists of β phase, in austenite form. The sample recovers its complete elongation up to a strain of 1% thanks to the transformation of the austenite/martensite phase during the elongation due to the stress and to its inverse transformation during unloading. During the elongation from 1% to 2.5%, the martensite/austenite inverse transformation is partial which explains the residual strains. The repeated austenite/martensite phase changes introduce defects into the material. These defects are responsible for localised elongation aspects and the conservation of martensite variants. Concerning sample A1, the ultimate strength is 240 MPa. No pseudoelastic behaviour is observed during the first strain cycle. This is correlated by the fact that the Ms martensitic transformation temperature (340K) is higher than the ambient temperature for this composition. The pseudoelastic behaviour which is then observed can be explained by the reversibility of the movement of the double boundaries in the martensite induced by the strain.

EXAMPLE 2

Figure 6:
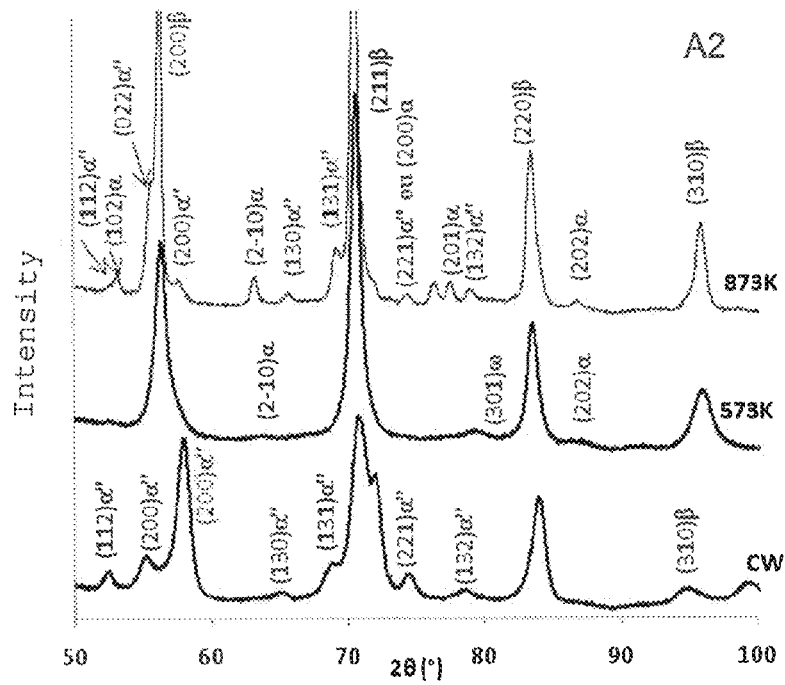
Figure 7:
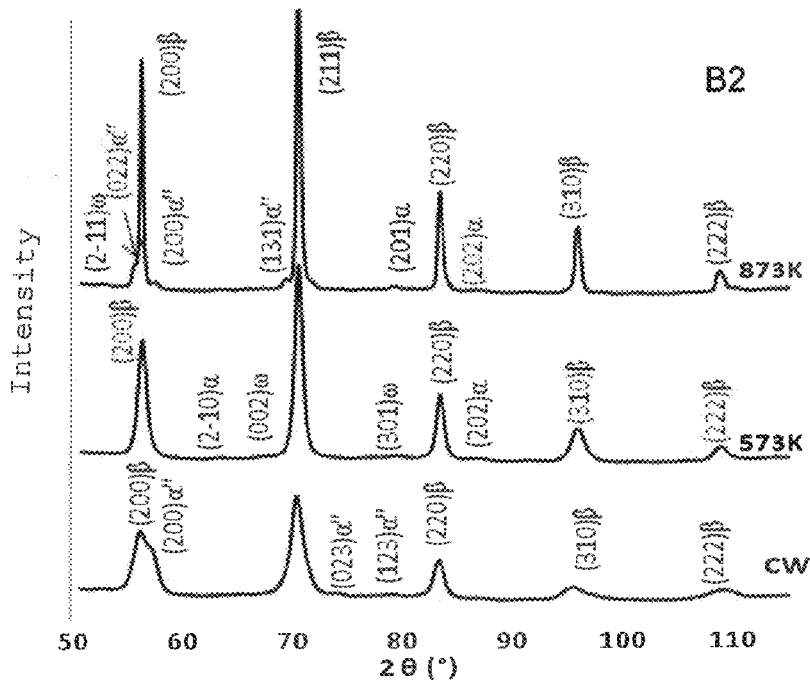

Samples from the process described in example 1 are submitted to a severe cold rolling applying a true strain greater than 3. Then they are submitted to a short ageing heat treatment of 10 minutes terminated by a water quench. Two temperature levels were explored: 573K and 873K (300 and 600° C.). FIG. 6 shows three X-ray diffraction diagrams for a sample A1 rolled and not aged (A2 CW), a sample A1 rolled and aged at 573K (A2 573K) and a sample A1 rolled and aged at 873K (A2 873K). Likewise, FIG. 7 shows three X-ray diffraction diagrams for a sample B1 rolled and not aged (B2 CW), a sample B1 rolled and aged at 573K (B2 573K) and a sample B1 rolled and aged at 873K (B2 873K).

The analysis of sample B2 CW shows the presence of β phase and α" martensite induced by the strain. For sample A2 573K, it can be seen that the inverse transformation of the martensite into austenite is almost complete, maintaining a high dislocation density. Traces of ω phase and α phase appear by the decomposition of the β metastable phase. For sample A2 873K, an α" phase is detected in addition to the α and β phases. Recent studies have established that the effect of the α phase precipitation was to extract the oxygen from the β phase matrix and increase the Ms martensitic transformation start temperature. This can explain the presence of martensitic phase after the fast cooling which follows the heat treatment at 873K, especially for sample B2 873K.

Figure 8:
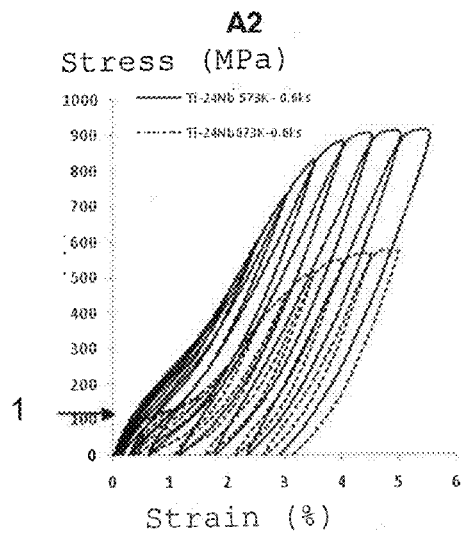
FIGS. 8 and 9 show the tension-release test curves for the samples of FIGS. 6 and 7, FIGS. 10 and 11 are diagrams showing respectively the Young's modulus and the recoverable strain for the samples of FIGS. 1, 2, 6 and 7, FIGS. 12 to 14 are diagrams respectively showing the Young's modulus, the strength and the recoverable strain versus the ageing heat treatment time.
Figure 9:
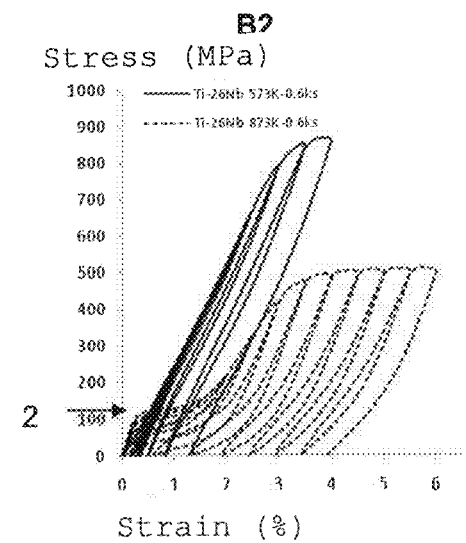

Mechanical characterisation tests were conducted by performing tension-release cycles with constant strain increments. The curves relating the strain to the stress are shown on FIG. 8 for samples A2 573K and A2 873K and on FIG. 9 for samples B2 573K and B2 873K. It can be seen that these curves show a mechanical behaviour which is much better than samples A1 and B1 after solution annealing and quenching. In particular, the superelastic properties are improved: samples A2 573K and B2 873K have a perfect superelastic behaviour after an imposed elongation of 2% at ambient temperature. The precipitation of fine α phase particles during the heat treatment probably influences the mechanical properties by its effect on the β phase and is responsible for the increase in the critical sliding stress. The critical stress of the martensite induced by the stress is not affected for sample A2 873K and decreases for sample B2 873K as shown by steps 1 and 2, in comparison with samples A1 and B1. The α phase precipitation increases the Ms temperature, favouring the formation of martensite induced by the stress, which can explain the reduction of the critical stress for the formation of martensite induced by the stress. Also, the small size of the grains caused by the severe cold strain contributes towards increasing the critical stress required for the plastic transformation (Hall-Petch effect). For samples A2 573K and B2 573K, the stress versus elongation curves show a non-linear elastic strain behaviour without double yield strength. The behaviour of these alloys is substantially different from those treated at 873K with, in addition, a sliding stress considerably higher and a superelasticity of around 2.5%.

Figure 10:
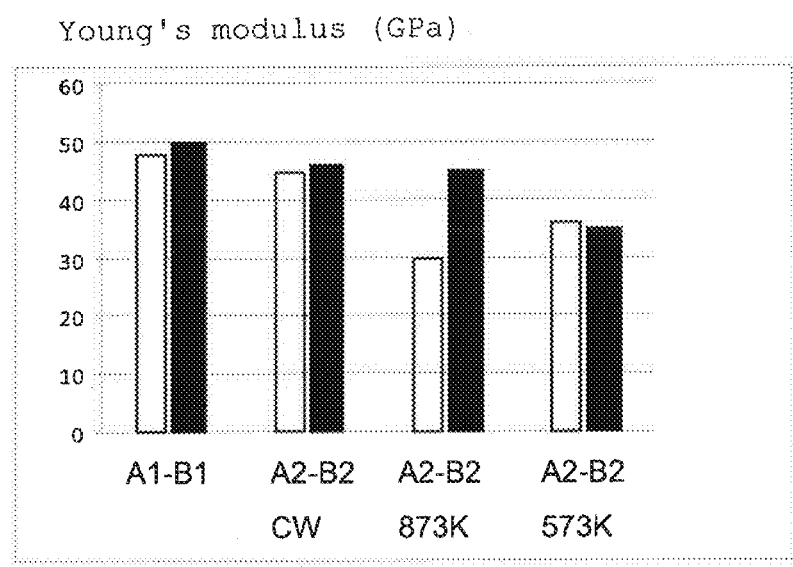

The Young's modulus (or modulus of elasticity) is defined as the slope of the tangent to the elongation-stress curve for a null stress. FIG. 10 shows the Young's modulus values for the various samples.

Figure 11:
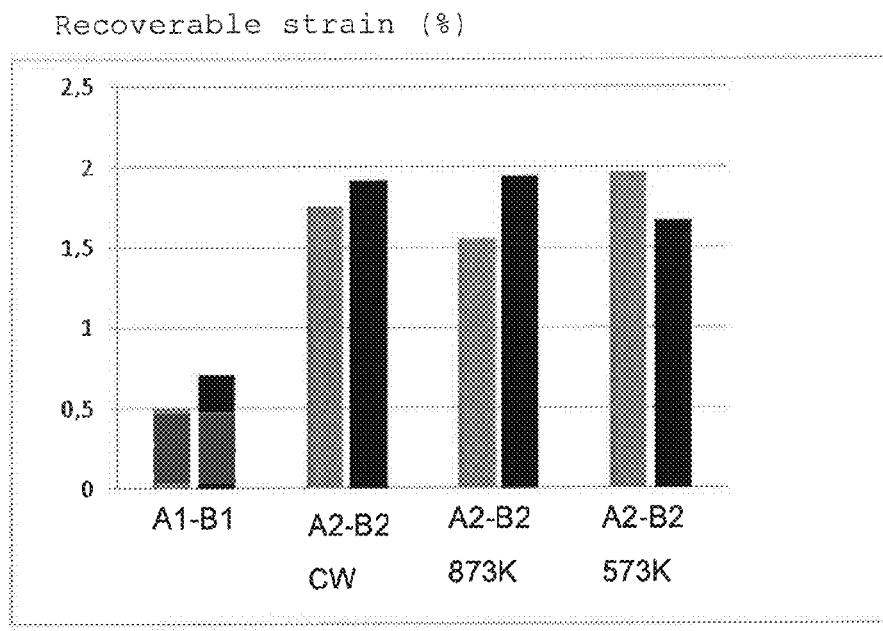

Moreover, FIG. 11 shows the recoverable strain $\epsilon_r$ for the same samples.

For the samples after cold rolling A2 CW and B2 CW, the Young's modulus is slightly lower than that of the samples after quench A1 and B1. After the heat treatment at 873K, the Young's modulus is 45 and 30 GPa respectively for samples A2 873K and B2 873K. After the heat treatment of 573K, the two alloys have a Young's modulus more or less identical at 35 GPa. It is interesting to note that the reduction in the Young's modulus after the heat treatment cannot be attributed to the volume fraction of α" martensite. Certain authors have indicated that the decrease in the Young's modulus of alloy TI-35Nb-4Sn (in mass proportion) by a cold strain of 89% would be due to an anisotropy of the Young's modulus of the α" martensite with the formation of texture $(200)_{\alpha"}[010]_{60"}$. After a heat treatment at 573K for 20 minutes, the Young's modulus increases slightly from 43 GPa to 53 GPa. The α-phase precipitate is known to increase the Young's modulus. However, the α-phase precipitate which appears during the heat treatment at 873K for 10 minutes is very small in size and in volume fraction. The lowering of the Young's modulus, the improvement in the superelastic behaviour and the increase in the strength maintain a low Young's modulus by the severe cold strain followed by a short heat treatment are not very well explained by the considerations on the changes in the microstructure.

EXAMPLE 3

Figure 12:
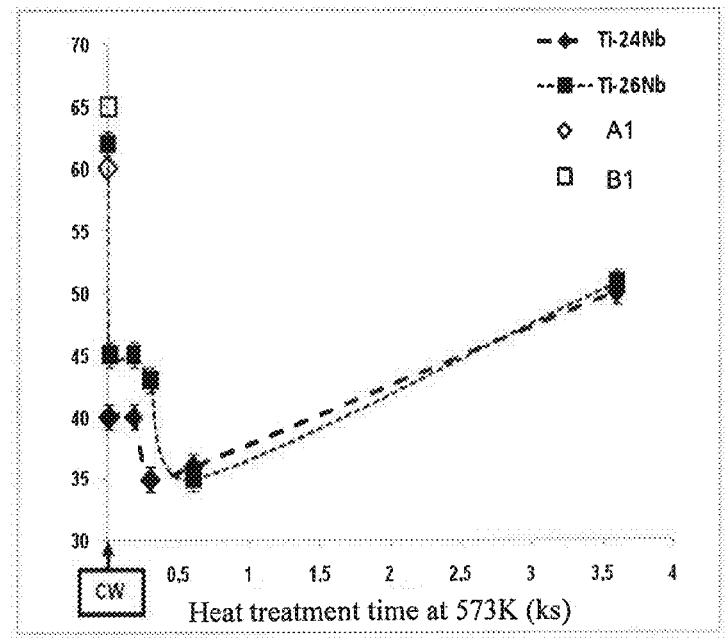
Figure 13:
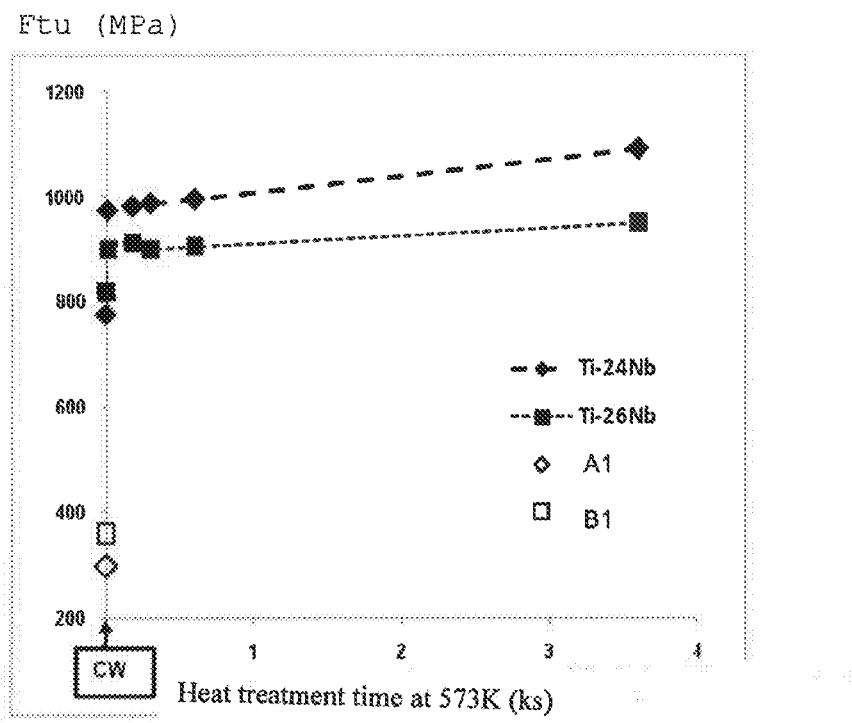
Figure 14:
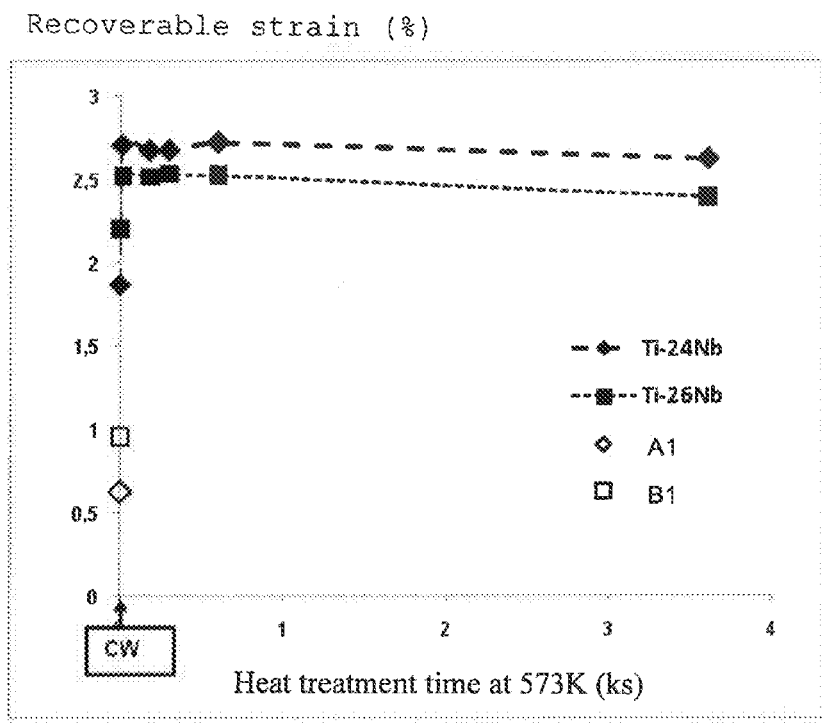

Samples have been made as in example 2, but by varying the ageing heat treatment time. The results for the values of the Young's modulus, the maximum strength and the recoverable strain for an imposed strain of 3% are shown respectively on FIGS. 12 to 14 versus the ageing time for a heat treatment at 573K. The examples 1 and 2 are also shown on these graphs by white diamond or square symbols. The first solid symbol on the ordinate axis corresponds to the state after cold rolling CW. The second symbol near to the ordinate axis corresponds to an ageing treatment of one minute. FIG. 12 shows that the reduction in the Young's modulus is obtained for a short ageing treatment time and that, when it is extended, the Young's modulus increases again. Only the reincrease of the modulus was known up until now. FIGS. 13 and 14 show that the maximum strength and the recoverable strain increase very quickly and then are affected only slightly by the increase in the heat treatment time even when the Young's modulus is low.

Figure 15:
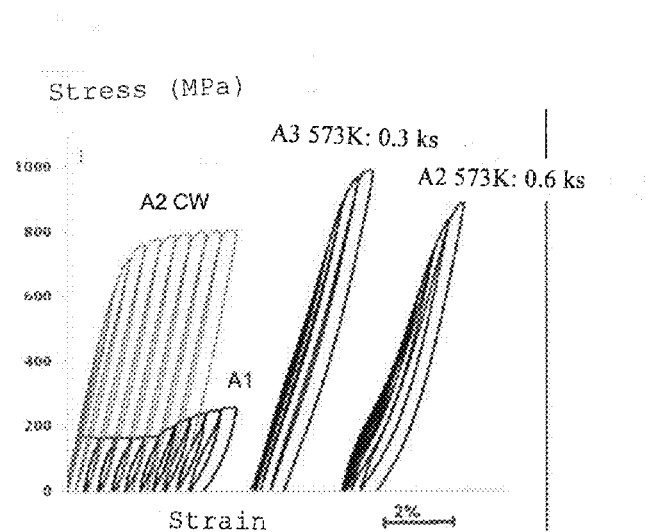
FIG. 15 shows a tension-release curve for a sample which was submitted to a heat treatment of 5 minutes compared with other samples.

FIG. 15 shows the tension-release test curves for the samples consisting of 24% niobium. The curves of samples A1, A2 CW and A2 573K are again reproduced for comparison with that of a sample A3 573K which has undergone an ageing heat treatment of 5 minutes (0.3 ks).

EXAMPLE 4

Samples including 0.5% oxygen or 0.5% nitrogen were prepared with 24% niobium in atomic weight according to the process described for example 1. These components have a betagenic effect, that is temperature Ms is lowered. These alloys have a β structure at ambient temperature, like sample B1. In comparison with sample B1, in the state after homogenisation treatment and quench, the mechanical strength is clearly improved, as shown by the results in table 1.

| Sample | Composition | Structure | Young's modulus (GPa) | Recoverable strain (%) | Maximum strength (MPa) | Elongation (%) |
| --- | --- | --- | --- | --- | --- | --- |
| C1 | Ti—24Nb—0.5O | β | 50 | 1.8 | 830 | 22 |
| D1 | Ti—24Nb—0.5N | β | 38 | 2.25 | 680 | 13 |
| B1 | Ti—26Nb— | β | 55 | 1 | 420 | 25 |

EXAMPLE 5

Figure 16:
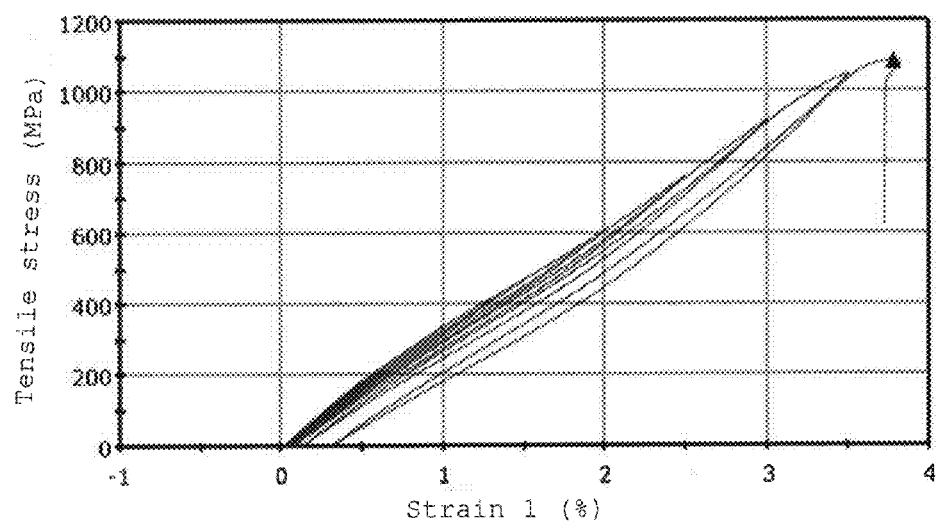
FIG. 16 shows a tension-release curve for a sample including zirconium.

A sample E2 is made with a composition of titanium, niobium (20%) and zirconium (6%, in atomic proportion) and with a thermomechanical treatment process as described in example 2, with an ageing heat treatment temperature of 600° C. for 10 minutes. FIG. 16 shows the tension-unload test curve. Such a sample E2 has a Young's modulus of 30 GPa and a maximum strength of 1100 MPa, with a recoverable strain of 3%.

EXAMPLE 6

Figure 17:
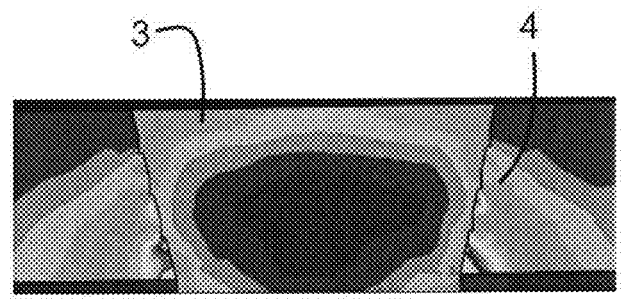
FIG. 17 shows a diagram representing the stress level for a dental implant placed in the bone of a jaw.
Figure 18:
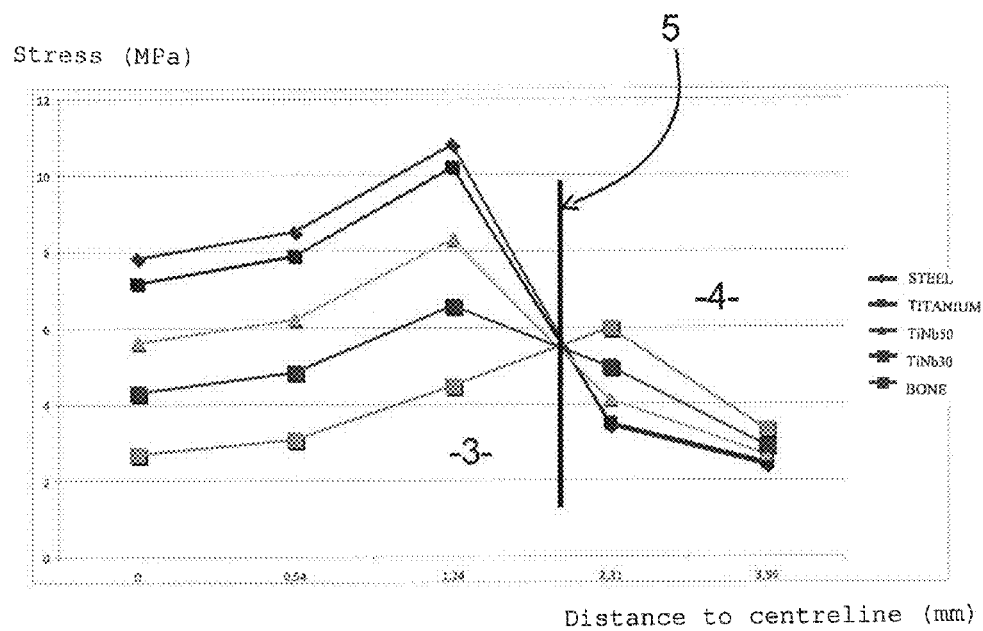
FIG. 18 shows a diagram representing the stress level according to a radius from FIG. 17 for different Young's modulii corresponding to different materials.
Figure 19:
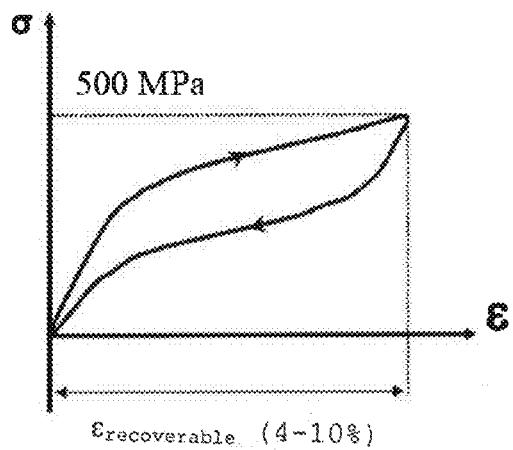
FIGS. 19 to 21 show tension-release test curves to illustrate various typical behaviours of superelastic or pseudoelastic materials.
Figure 20:
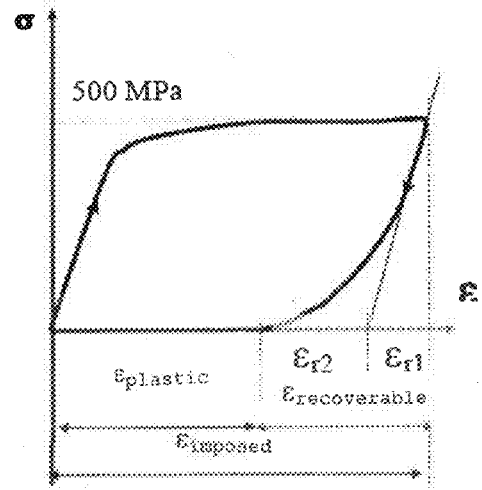
Figure 21:
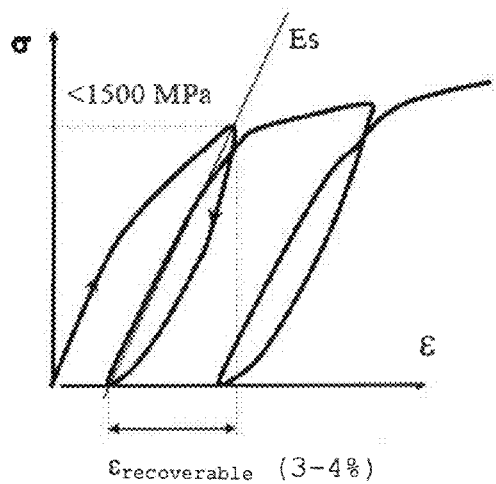

A numerical simulation of the structure of a dental implant 3 in the bone 4 of a jaw was done, varying the Young's modulus of the implant. The Young's modulus of the bone was simulated at 20 GPa. FIG. 17 shows an example of the distribution of the stresses between the implant 3 and the bone 4. FIG. 18 shows the plot of the stress level along a radius normal to the surface of junction 3 between the implant and the bone for various implant materials. The values of the Young's modulii have been chosen as follows:
Steel: 210 GPa
Titanium: 110 GPa
TiNb50: 50 GPa
TiNb30: 30 GPa
Bone: 15 GPa It can be seen that the step in the stress, on either side of the junction surface 5, is greatly reduced with niobium alloys compared with steel or pure titanium. This corresponds to a reduction of the stress deviation which leads to less bone losses around the implant. Even if the value of the Young's modulus is divided by two between steel and titanium, the stress deviation remains high in both cases. However, a substantial difference can be seen between a modulus of 50 GPa and a modulus of 30 GPa.

The invention claimed is:

1. Thermomechanical treatment process for a titanium alloy including between 23 and 27% niobium, between 0 and 10% zirconium, and between 0 and 1% oxygen, nitrogen and/or silicon, the ratios being expressed in atomic proportions, process wherein the following steps are performed:
    a) an increase in temperature of a sample of the alloy to a temperature higher than 900° C.,
    b) a fast quench,
    c) a cold strain higher than a true strain of 3,
    d) an ageing treatment at a temperature included between 200 and 600° C., the ageing treatment time being included between 10 seconds and 10 minutes.

2. Process according to claim 1, wherein step a) is preceded by a homogenisation step at a temperature higher than 1200° C. for at least 20 hours.

3. Process according to claim 1, wherein, at step c), the strain is done only on the surface of a sample.

4. Titanium alloy including between 23 and 27% niobium in atomic proportion, between 0 and 10% zirconium, and between 0 and 1% oxygen, nitrogen and/or silicon, characterised in that it is obtained by the process according to claim 1 and that its Young's modulus is lower than 45 GPa.

5. Alloy according to claim 4, wherein the ratio of niobium is between 24% and 26% in atomic proportion.

6. Alloy according to claim 5, wherein the ratio of niobium is 24%, the crystallographic structure being β phase with traces of α martensite and a ω phase after ageing treatment at 300° C.

7. Alloy according to claim 5, wherein the niobium ratio is 24%, the crystallographic structure including a β phase, α martensite and α″ martensite after an ageing treatment at 600° C.

8. Alloy according to claim 5, wherein the niobium ratio is 26%, the crystallographic structure including a β phase and α″ martensite.

9. Alloy according to claim 4, wherein the zirconium ratio is 0%.

10. Prosthesis implantable in a human or animal body, characterised in that it is made from an alloy according to claim 4.

11. Dental implant according to claim 10.

* * * * *